United States Patent
van Krieken et al.

(10) Patent No.: US 7,332,085 B2
(45) Date of Patent: Feb. 19, 2008

(54) METHOD FOR THE PURIFICATION OF AN α-HYDROXY ACID ON AN INDUSTRIAL SCALE

(75) Inventors: Jan van Krieken, Gorinchem (NL); Jan van Breugel, Woudrichem (NL)

(73) Assignee: Purac Biochem B.V., Gorinchem (NL)

( * ) Notice: Subject to any disclaimer, the term of this patent is extended or adjusted under 35 U.S.C. 154(b) by 173 days.

(21) Appl. No.: 10/380,537

(22) PCT Filed: Sep. 14, 2001

(86) PCT No.: PCT/NL01/00683

§ 371 (c)(1), (2), (4) Date: Jan. 14, 2004

(87) PCT Pub. No.: WO02/22545

PCT Pub. Date: Mar. 21, 2002

(65) Prior Publication Data

US 2004/0129635 A1   Jul. 8, 2004

(30) Foreign Application Priority Data

Sep. 15, 2000   (NL) ................................. 1016202

(51) Int. Cl.
  *B01D 11/00*   (2006.01)
  *B01D 9/02*   (2006.01)
  *B01D 1/00*   (2006.01)

(52) U.S. Cl. ............... 210/634; 23/299; 159/47.1; 159/49; 210/639; 210/774; 210/806; 435/139; 562/580; 562/589

(58) Field of Classification Search ............... 210/634, 210/639, 774, 806; 34/282, 427; 203/39, 203/48; 435/139, 853–857; 562/578–580, 562/593, 589; 23/299; 159/47.1, 47.3, 49; 426/34, 41–43
See application file for complete search history.

(56) References Cited

U.S. PATENT DOCUMENTS

| 2,474,046 | A | * | 6/1949 | Fries ........................... 435/139 |
| 2,967,880 | A | * | 1/1961 | Finke et al. ................. 560/164 |
| 3,284,495 | A | * | 11/1966 | Vogt et al. ................... 562/589 |
| 4,698,303 | A | * | 10/1987 | Bailey et al. ................ 435/139 |
| 5,426,219 | A | * | 6/1995 | Lehnhardt et al. ......... 562/589 |
| 5,510,526 | A | | 4/1996 | Baniel et al. |
| 5,859,296 | A | | 1/1999 | Neuamann et al. |
| 6,229,046 | B1 | * | 5/2001 | Eyal et al. .................. 435/139 |

FOREIGN PATENT DOCUMENTS

| DE | 593657 | 2/1934 |
| EP | 0 159 585 B1 | 10/1985 |
| EP | 0 563 455 A1 | 10/1993 |
| JP | 07-033704 A | 2/1995 |
| JP | 09-067300 A | 3/1997 |
| NL | 1013265 C2 | 4/2001 |
| NL | 1013682 C2 | 5/2001 |
| WO | WO 92/05138 | 4/1992 |
| WO | WO 99/19290 | 4/1999 |
| WO | WO 00/56693 | 9/2000 |

OTHER PUBLICATIONS

Loree J. Poole and C. Judson King, "Regeneration of Carboxylic Acid-Amine Extracts by Back-Extraction with an Aqueous Solution of a Volatile Amine", Ind. Eng. Chem. Res. 1991, vol. 30, pp. 923-929, published by American Chemical Society in 1991.*
W.G. Kerckhoff, "The preparation of Crystalline Lactic Acid", Jun. 7, 1933, pp. 449-460.
Ullmans Encyklopadie der Technischen Chemie, Verlag Chemie GmbH, Weinheim, fourth edition, Part 17, pp. 1-7 (1979).
The Merck Index, Merck & Co., Inc., eleventh edition, p. 842 (1989).
Rommp Chemie Lexicon, G. Thieme Verlag, Stuttgart and New York ninth edition, pp. 2616-2617 (1991).
Lockwood et al., N.Y. Acad. Sci. 119, 854 (1965).
Buszko et al., Mol. Phys. 76, 83-87 (1992).
Ing, et al., Int. J. Artif. Organs 17, 70-73 (1994).
Schouten et al., J. Mol. Struct. 323, 165-168 (1994).

* cited by examiner

*Primary Examiner*—Joseph Drodge
(74) *Attorney, Agent, or Firm*—Gilberto M. Villacorta; Sunit Talapatra; Foley & Lardner LLP

(57) ABSTRACT

The present invention relates to a method for the purification of an α-hydroxy acid on an industrial scale, in which the method involves: (a) subjecting an aqueous stream containing mainly α-hydroxy (1) to an extraction step, with the formation of an aqueous place containing mainly α-hydroxy acid (2), (b) concentrating the aqueous phase containing mainly α-hydroxy acid (2) by means of evaporation of water under reduced pressure, with the formation of a concentrated α-hydroxy acid solution in water (3), and (c) subjecting the concentrated α-hydroxy acid solution (3) to a crystallization, with formation of pure α-hydroxy acid (4), where (i) the concentrated α-hydroxy acid solution (3) is directly cooled in a melting crystallization device, and/or (ii) the concentrated α-hydroxy acid solution (3) is diluted with water and crystallization is brought about in one or more cooling crystallization devices and/or evaporative crystallization devices, and/or (iii) crystallization is brought about in one or more adiabatic crystallization devices.

26 Claims, No Drawings

METHOD FOR THE PURIFICATION OF AN α-HYDROXY ACID ON AN INDUSTRIAL SCALE

The present invention relates to a method for the purification of α-hydroxy acids, in particular lactic acid or glycolic acid, on an industrial scale, as well as to products of the utmost chiral purity which can be obtained by this method, and to applications thereof.

Lactic acid is usually marketed as a dilute or concentrated solution, because lactic acid has a strong tendency to form intermolecular esters (dimeric and polymeric lactic acid). In addition, lactic acid (even very pure lactic acid) is strongly hygroscopic. The purification of lactic acid (the racemic mixture and in particular the enantiomers of lactic acid) on an industrial scale is a complicated and difficult process according to the prior art.

It is known how to produce lactic acid, or 2-hydroxypropionic acid, in a fermentative manner. In general the fermentative production of lactic acid includes first of all a fermentation step in which a carbohydrate-containing substrate such as glucose or sucrose is converted to lactic acid by a suitable microorganism. Known microorganisms producing (S)-lactic acid are various bacteria of the genus *Lactobacillus*, such as *Lactobacillus casei* for example. In addition microorganisms are also known which produce (R)-lactic acid selectively. The aqueous fermentation product is then processed in order to obtain lactic acid. The usual industrial processing path generally consists of separation of the biomass followed by acidification, purification and concentration.

In the case of (S)-lactic acid the lactic acid so obtained is sufficiently pure to be processed in foods for human consumption. (S)-or (R)-lactic acid which is ultimately obtained by this usual method can be 98% enantiomerically pure or even higher (i.e. 98% or more of the lactic acid present consists of the (S) or (R) enantiomer). The product still contains residual sugars, however. The product is also yellow in colour and on heating this becomes brown to black through decomposition of impurities. Moreover, in the case of (S)-lactic acid, the organoleptic properties often leave something to be desired. The lactic acid enantiomer is thus moderately suitable for application in foods, but on the whole not suitable for pharmaceutical applications and for synthesis of chiral compounds.

The purity of the product can be increased by esterification followed by hydrolysis, so that it is suitable for pharmaceutical applications. As a result of this esterification/hydrolysis, however, the enantiomeric purity decreases and the lactic acid still contains a small amount of the alcohol which bas been used in the esterification. Examples of other methods for the purification of lactic acid include subjecting aqueous solutions of lactic acid to one or more extraction, (steam) distillation and/or evaporation steps, electrodialysis steps and crystallizations (see for example Ullmans Encyklopädie der Technischen Chemie, Verlag Chemie GmbH, Weinheim, fourth edition, Part 17, pages 1-7 (1979); H. Benninga, "History of Lactic Acid Making", Kluwer Academic Publishers, Dordrecht-Boston-London (1990); C. H. Holten, "Lactic Acid; Properties and Chemistry of Lactic Acid and Derivatives", Verlag Chemie GmbH, Weinheim (1971); The Merck Index, Merck & Co., Inc., eleventh edition page 842 (1989); Römmp Chemie Lexicon, G. Thieme Verlag, Stuttgart and New York, ninth edition, Part 4, pages 2792-2893 (1991) and the Netherlands patent applications 1013265 and 1013682.

In German Patent 593,657 (granted on 15 Feb. 1934) a laboratory experiment is described in which an aqueous solution of lactic acid, which contained an excess of the (S) component and practically no lactic acid anhydride, was concentrated by means of a thin-film evaporation technique, if necessary at reduced pressure. The concentrated lactic acid solution was then rapidly cooled, with formation of crystals. After that the crystals were separated from the mother liquor, washed with ether and repeatedly recrystallized from ethyl acetate or chloroform or a comparable solvent until the crystals showed a sharp melting point of 53° C. The chiral purity or the enantiomeric excess and the colour are not reported.

In H. Borsook, H. M. Huffman, Y-P. Liu, J. Biol. Chem. 102, 449-460 (1933) a laboratory experiment is described in which an aqueous mixture, which contained 50 percent lactic acid with an excess of (S)-lactic acid, 30 percent lactic acid anhydride and lactic acid dimer and 15percent water, was subjected to fractional distillation at approximately 0.13 mbar and 105° C. The middle fraction was then distilled again and after that cooled in an ice/salt bath with formation of a solid crystal mass. It is reported that the distillation has to be performed with small quantities, because with larger quantities there is a big loss of product as a result of the long heating time. The solid crystal mass was then recrystallized three times from an equal volume of equal quantities of diethyl ether a diisopropyl ether, and the crystals were isolated and died at room temperature in a vacuum drier. In this way it was possible to obtain (S)-lactic acid with a melting point of 52.7-52.8° C. which contained less than 0.1 percent impurities such as water, lactic acid anhydride or lactic acid dimer. The chiral purity or the enantiomeric excess and the colour of (S)-lactic acid are not reported.

In L. B. Lockwood, D. E. Yoder, M. Zienty, Ann. N.Y. Acad. Sci. 119, 854 (1965) the distillation and crystallization of lactic acid on a laboratory scale is also described, the melting point of the optically pure lactic acid obtained being 54° C. The colour is not reported.

In 1934 the crystallization of lactic acid was investigated by Boehringer Ingelheim, but this method was not found to give good results, owing to problems with the purification and further treatment. After the Second World War, however, it turned out that Boehringer Ingelheim was able to produce lactic acid for pharmaceutical applications on a scale of about 12 to 15 tons per month, with a yield of about 77 to 86 percent. In this process an aqueous solution of lactic acid was purified by means of steam distillation at reduced pressure (about 13 mbar), followed by crystallization at −25° C., after which the crystals were dissolved in water and the solution was treated with potassium ferrocyanide (to remove heavy metals) and activated charcoal. The chiral purity or the enantiomeric excess or other properties such as colour and odour of the (S)-lactic acid so produced are not known (see H. Benninga, "History of Lactic Acid Making", Kluwer Academic Publishers, Dordrecht-Boston-London, pages 347-350 (1990)).

Crystalline (S)-lactic acid has been marketed by, for example, Fluka and Sigma with purities of more than 99% (see for example M. L. Buszko, E. R. Andrew, Mol. Phys. 76, 83-87 (1992) and T. S. Ing, A. W. Yu, V. Nagaraja, N. A. Amin, S. Ayache, V. C. Gandhi, J. T. Daugirdas, Int. J. Artif. Organs 17, 70-73 (1994)). Crystalline (S)-lactic acid with a water content of less than 1 percent by weight is known from EP A 563,455 (see Example 1). The crystal structure of lactic acid is decribed in A. Schouten, J. A. Kanters, J. van Krieken, J. Mol. Struct. 323, 165-168 (1994).

Lactic acid can also be obtained in a synthetic manner. This is known. The product of the synthetic production method, however, is a racemic mixture which thus contains (S)-lactic acid and (R)-lactic acid in equal quantities. It is true that the separate enantiomers can be separated by means of known techniques, such as diastereoisomer separation techniques, where one of the enantiomers crystallizes out as a salt and this salt is then converted back to the enantiomeric lactic acid, but the enantiomeric product finally obtained will inevitably still contain significant quantities of the other enantiomer.

In European Patent Application 552,255 it is reported that glycolic acid of industrial quality can be crystallized by putting a solution thereof in a freezer, giving rise to crystals which are filtered off. It will be clear that such a method is unsuitable for being carried out on an industrial scale. Such a method is also applied in DE A 2,910,975.

In WO 00/56693 a method is described for the purification of lactic acid on an industrial scale, the method involving: (a) the distillation under reduced pressure of a concentrated lactic acid solution with a total acid content of at least 95% by weight and a monomeric lactic acid content of at least 80% by weight, calcuated in terms of the concentrated lactic acid solution, and with a ratio of the lactic acid enantiomers not equal to 1, and (b) subjecting the distilled lactic acid solution to a crystallization, with formation of pure lactic acid, where the pure lactic acid has a total acid content of at least 99% by weight, a monomeric lactic acid content of at least 98% by weight, a chiral purity of 99% or more, calculated in terms of the total quantity of pure lactic acid, a colour of not more than 10 APHA units and an acceptable odour.

Disadvantages of this method are that step (a) produces a quantity of residue which is of the order of 5-10% by weight of the total quantity of lactic acid that is present in the feed. The yield, although not low, can be improved. Step (b) of this method provides about 45% by weight of end product, calculated in terms of the feed of step (a), and approximately 45% by weight of mother liquor, which is relatively pure.

The present invention aims to improve the yield of the method according to WO 00/56693, in particular the yield of step (a). In addition, it has been found that not only lactic acid but also other α-hydroxy acids such as glycolic acid can very effectively be purified by the method according to the present invention.

The present invention therefore relates to a method for the purification of an α-hydroxy acid on an industrial scale (i.e. a scale of at least 1000 tons per annum), with the method involving:
  (a) subjecting an aqueous stream containing mainly α-hydroxy acid [1] to an extraction step, with the formation of an aqueous phase containing mainly α-hydroxy acid [2],
  (b) concentrating the aqueous phase containing mainly α-hydroxy acid [2] by means of evaporation of water under reduced pressure, with the formation of a concentrated α-hydroxy acid solution in water [3], and
  (c) subjecting the concentrated α-hydroxy acid solution [3] to a crystallization, with formation of pure α-hydroxy acid [4], where the pure α-hydroxy acid has a total acid content of at least 99% by weight, a monomeric α-hydroxy acid content of at least 98% by weight and, if applicable, a chiral purity of 99% or more, calculated in terms of the total quantity of pure α-hydroxy acid, and a colour of not more than 10 APHA units and an acceptable odour.

An α-hydroxy acid means a carbonic acid which is substituted with a -hydroxy group on the α carbon atom. The general formula of an α-hydroxy acid is therefore:

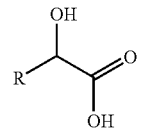

where R is a hydrogen atom, a $C_1$-$C_5$ alkyl group (preferably a methyl group), a $C_6$-$C_{12}$ aryl group or a heterocyclic cycloalkyl or -aryl group. The α-hydroxy acid according to the invention is preferably lactic acid (R is methyl) or glycolic acid (R is hydrogen) and is in particular lactic acid.

It has been found that the yield of this method is higher than that according to WO 00/56693. In step (a) of the method according to the present invention there is considerably less loss than in step (a) of the method according to WO 00/56693, i.e. less than 5% by weight of the α-hydroxy of the feed, calculated in terms of the whole feed, is lost as raffinate. Step (b) of the present method is also described in WO 00/56693 for the preparation of the feed of step (a) of the method described therein. In addition, step (c) of the present method produces a mother liquor which is relatively pure and can easily be purified to α-hydroxy acid for applications which require less pure product, e.g. foods. On the other hand, the α-hydroxy acid which is obtained by the present method is extremely pure and highly suitable for pharmaceutical applications.

According to the invention, step (a) comprises the following component steps:
  (i) subjecting an aqueous stream containing mainly α-hydroxy acid [1] to a first extraction step, where the aqueous stream containing mainly α-hydroxy acid [1] is brought into contact with a stream which is mainly insoluble in water and which contains an extraction agent [5], with the formation of an organic phase containing mainly α-hydroxy acid and extraction agent [6] and a first aqueous phase containing mainly contaminants [7], and
  (ii) subjecting the organic phase containing mainly α-hydroxy acid and extraction agent [6] to a second extraction step, where the organic phase containing mainly α-hydroxy acid and extraction agent [6] is brought into contact with an aqueous stream [8] with the formation of an aqueous phase containing mainly α-hydroxy acid [2] and an organic phase containing mainly extraction agent [9], with the organic phase containing mainly extraction agent [9] being fed back to step (i).

The aqueous stream containing mainly α-hydroxy acid [1] preferably contains 0.1 to 25% by weight α-hydroxy acid, calculated in terms of the whole stream.

The aqueous phase containing mainly α-hydroxy acid [2] preferably contains 0.1 to 25% by weight α-hydroxy acid, calculated in terms of the whole aqueous phase, and has a colour which is preferably not more than 100 APHA units and in particular not more than 60 APHA units. On the other hand, stream [2] can be a concentrated stream which contains 30 to 80% by weight, preferably 30 to 50% by weight α-hydroxy acid, calculated in terms of the whole stream, with this stream having a colour which is preferably not more than 200 APHA. If such a concentrated stream [2] is applied, this has the advantage that the first aqueous phase containing mainly contaminants [7] can be discharged without further purification or further treatment.

The concentrated α-hydroxy acid solution [3] preferably has a total acid content of at least 70% by weight, more preferably at least 80% by weight and in particular at least 85 to 95% by weight, calculated in terms of the whole concentrated α-hydroxy acid solution [3].

If the α-hydroxy acid is lactic acid, stream [3] preferably has a total acid content of at least 80% by weight, more preferably at least 90% by weight and in particular 90 to 95% by weight. The chiral purity of the solution is then at least 90%, more preferably at least 95% and in particular at least 98%.

If the α-hydroxy acid is glycolic acid, stream [3] preferably has a total acid content of at least 70% by weight, more preferably at least 80% by weight and in particular 85 to 95% by weight. As will be clear to the expert, in the case of glycolic acid the chirality is unimportant.

Total acid content (TA) is the acid content after saponification of intermolecular ester bonds with an excess base and is determined by back titration with acid. The total acid content thus gives the quantity of monomeric, dimeric and polymeric lactic acid and is expressed as the percentage by weight of monomeric lactic acid. The free acid content (FA) is determined by direct titration with base, i.e. before saponification of the intermolecular ester groups. The content of monomeric lactic acid (MM) is here defined as:

$$MM=TA-2\times(TA-FA)$$

provided that TA−FA<10%. This means that not very much dimeric or polymeric lactic acid can be present. It is also assumed that the non-monomeric lactic acid is present in the form of lactoyl lactic acid (dimer).

Chiral purity (for an excess (S)-isomer) is here defined as:

$$\text{Chiral purity}=100\%\times\{((S)\text{-isomer})/(R)\text{-isomer}+(S)\text{-isomer})\}$$

With the method according to the invention an α-hydroxy acid can be obtained which is both colourless and chirally pure. The degree of coloration is determined in accordance with ASTM D 5386-93 and is expressed in "APHA units". The method is suitable for determining coloration of clear liquids. A coloration of at least 10 APHA units means that the relevant liquid has a visually imperceptible coloration and is thus colourless as observed with the naked eye. The coloration is also determined after hearing (for approximately two hours under reflux).

Advantages of the present invention are that α-hydroxy acid can be obtained with a high purity and with a high yield per unit of weight of the supplied feed per unit of time. In addition, with the method according to the present invention, α-hydroxy acid can be obtained with a colour (after heating for two hours under reflux cooling, of not more than 50 APHA, preferably not more than 25 APHA and in particular not more than 10 APHA (these values apply to an α-hydroxy acid solution which contains 92% by weight pure α-hydroxy acid). Another advantage of the present invention is that the first extraction step (i) of step (a) can be performed under atmospheric pressure. A further advantage of working at atmospheric pressure during the extraction is a short response time (the system rapidly reaches equilibrium), as a result of which the method can be effectively monitored and effectively controlled and is less sensitive to interference. In addition, it is easier to scale up the method to a large-scale industrial process. Finally, the extraction is simpler than corresponding extractions which are known from the prior art, because only liquid/liquid systems are involved and it has been found that relatively impure aqueous streams containing α-hydroxy acid, i.e. streams which for example contain large amounts of residual sugars, can be efficiently purified in this way.

FIG. 1 shows a preferred embodiment of the process according to the invention.

According to FIG. 1, an aqueous stream containing mainly α-hydroxy acid [1] is subjected to a first extraction, with stream [5] containing the extraction agent. The α-hydroxy acid is thus extracted from the aqueous phase to the organic phase (stream [6]), with the aqueous phase mainly containing contaminants and a small quantity of α-hydroxy acid (stream [7]). Stream [6] is subjected to a second extraction with the formation of an aqueous phase containing mainly α-hydroxy acid (stream [2]) and an organic phase containing mainly extraction agent [9]. Finally stream [2] is concentrated by evaporation of water, forming the concentrated α-hydroxy solution in water [3].

According to FIG. 1, stream [6] is subjected to a washing step with water, in which any remaining contaminants soluble in water are removed from the organic phase containing α-hydroxy acid. In this washing step it is unavoidable that a small quantity of α-hydroxy acid is also washed out of the organic phase (stream [6]), so that stream [10] is preferably fed back into the process, in particular before step (a) of the present method. Furthermore, the organic phase, containing mainly extraction agent, which is formed after the second extraction (stream [9]) is preferably washed with an aqueous solution of an inorganic base of an alkali metal, preferably sodium hydroxide, in order to remove any acid and other contaminants still present from stream [9]. The stream so purified [9] can be used again for the first extraction, i.e. be applied as a feed for stream [5]. In the purification of stream [9] an aqueous stream [11] is released which is discharged as a waste stream.

The aqueous stream [7] which is formed during the first extraction step (forward extraction) preferably contains at least 90% by weight water, calculated in terms of the complete mixture, and in particular at least 95% by weight water. In addition, stream [7]preferably contains not more than 5% by weight α-hydroxy acid. For an efficient extraction stream [7] is therefore fed back into the process before step (a). In addition, the first aqueous phase containing mainly contaminants [7] is concentrated by evaporation of water before this stream is further processed, either as a waste stream or as a feedback stream.

According to another preferred embodiment of the invention, the concentration of stream [7] can be omitted. In this case a concentration step is performed before step (a), with stream [1] being concentrated in such a way that an aqueous stream containing concentrated α-hydroxy acid is obtained which contains 40 to 50% by weight α-hydroxy acid, calculated in terms of the whole stream. This aqueous stream containing concentrated αhydroxy acid is then subjected to the first extraction step, with a stream [7] being formed which contains mainly only water and contaminants.

Step (i) of the method according to the invention is preferably carried out at atmospheric pressure and at a temperature of 0° to 60° C. in particular at a temperature of 10° and 50° C. If the extraction agent does not contain any alcohol and/or ketone, however, step (i) is preferably carried out at atmospheric pressure and at a temperature of 60° to 100° C. The volumetric ratio of the aqueous stream containing mainly α-hydroxy acid [1] and the mainly water-insoluble stream containing the extraction agent [5] is preferably between 20:1 and 1:20, more preferably between 3:1 and 1:7 and in particular between 2:1 and 1:5.

Step (ii) of the method according to the invention is preferably carried out at a pressure of 1 to 10 bar, in particular at a pressure of 2 to 9 bar, and a temperature of 100° C. to 180° C., in particular a temperature of 120° and 160° C. The volumetric ratio of the organic phase containing mainly α-hydroxy acid and extraction agent [6] and the aqueous stream [8]—step (ii)—is preferably between 20:1 and 1:20, more preferably between 3:1 and 1:7 and in particular between 2:1 and 1:5, and especially between 1:2 and 1:4.

The extraction agent which is used in step (i) of the method according to the present invention preferably comprises (1) an amine and (2) a hydrocarbon. The extraction agent preferably also comprises (3) an alcohol and/or a ketone. It has furthermore been found that good results can also be achieved with isopropyl ether, as is described for example in U.S. Pat. No. 1,906,068, which is here recorded for reference purposes. As has been noted, the conditions under which step (i) of the method according to the invention is carried out are various. If the extraction agent does not contain any alcohol and/or ketone, step (i) is preferably carried out at atmospheric pressure and at a temperature of 60° to 100° C. Otherwise step (i) is preferably carried out at atmospheric pressure and at a temperature of 0° to 60° C., in particular at a temperature of 10° and 50° C.

The amine is preferably a tertiary amine with at least 18 carbon atoms and preferably contains 24 to 42 carbon atoms. If the extraction agent contains an alcohol, which is preferable, the alcohol is a $C_8$-$C_{12}$ alcohol.

The hydrocarbon is preferably a petroleum fraction which consists of saturated alkanes and preferably has a flash point of at least 40° C., more preferably of at least 70° C. and in particular a flash point of at least 90° C. A higher flash point has the advantage that less stringent safety requirements need to be set for the equipment used in step (a). The boiling range of the hydrocarbon is preferably 150° to 275° C., in particular 170° to 260° C. The hydrocarbon is in particular Isopar K™ or Isopar M™.

The extraction agent preferably contains 40 to 75% by weight (1), 5 to 60% by weight (2) and 0 to 25% by weight (3), and in particular 45 to 55% by weight (1), 45 to 55% by weight (2) and 0 to 10% by weight (3).

Step (b) of the method according to the invention is preferably carried out in one or more falling-film evaporators and/or thin-film evaporators and/or smeared-film evaporators, with step (b) preferably being carried out at atmospheric pressure to a pressure of 0.1 bar, in particular 0.8 to 0.2 bar and at a temperature from 25° to 140° C., more preferably from 40° to 100° C. and in particular 60° to 85° C. Stream [2] is preferably at a pressure from 0.5 to 1 bar, in particular from 0.7 to 0.9 bar, and a temperature of 50° to 100° C., in particular from 70° to 90° C.

The known crystallization techniques can in principle be applied in step (c). An example of such a technique is melting crystallization (or cooling crystallization), where the condensed, liquid concentrate or distillate, which for example contains the (S)-α-hydroxy acid or (R)-α-hydroxy acid in a molten state, is directly cooled, so that the (S)- or (R)-α-hydroxy acid crystallizes out. It is preferable to keep the temperature at which crystallization occurs (the crystallization temperature) as low as possible, so that the formation of oligomers and polymers of the α-hydroxy acid is limited as much as possible.

Melting crystallization is a process in which a crystalline material is obtained from a melt of the material to be crystallized. This technique is for example described in detail in Kirk-Othmer, Encyclopedia of Chemical Technology, fourth edition, Part 7, pages 723-727 (1993), in J. W. Mullin, "Crystallization", third revised edition, Butterworth-Heinemann Ltd., pages 309-323 (1993) and in J. Ullrich and B. Kallies, Current Topics in Crystal Growth Research, 1 (1994), which have been recorded here for reference. The main advantage of melting crystallization relative to distillation is that much less energy is needed, because the enthalpy of melting of organic compounds is generally lower than the enthalpy of evaporation. This advantage also occurs with other crystallization techniques, because the enthalpy of crystallization is usually lower than the enthalpy of evaporation. Another advantage of melting crystallization relative to distillation is furthermore that the process can generally be carried out at a much lower temperature—which is advantageous when the organic compound is thermally unstable.

The melting crystallization can be carried out with the aid of a suspension crystallization or a layer crystallization, if necessary in combination with a washing column or a centrifuge, or another purification technique. Examples of suitable equipment and processes are described in Kirk-Othmer, Encyclopedia of Chemical Technology, fourth edition, Part 7, pages 723-727 (1993), in J. W. Mullin, "Crystallization", third revised edition, Butterworth-Heinemann Ltd., pages 309-323 (1993) and J. Ullrich and B. Kallies, Current Topics in Crystal Growth Research, 1 (1994), the content of which has been recorded here for reference.

It has also been found that crystallization of an aqueous solution gives very good results. In this crystallization treatment the concentrated lactic acid solution is diluted with water and this is then subjected to one or more cooling and/or evaporative crystallization steps. In these techniques the concentrate or distillate is directly cooled (cooling crystallization) or concentrated by evaporation of water (evaporative crystallization). The driving force for the crystallization in the cooling crystallization technique is the bringing about of supersaturation in the concentrated lactic acid solution by reducing temperature of the concentrated lactic acid solution. As a result of the lower temperature of the solution the solubility decreases and supersaturation occurs.

The driving force for the crystallization in the evaporative crystallization technique is the bringing about of supersaturation in the concentrated lactic acid solution by evaporation of water, as a result of which the concentration of the solution increases while the temperature remains constant. Crystallization of the lactic acid then occurs during the evaporation of water.

Another highly stable crystallization technique is adiabatic crystallization, where the driving force for the crystallization is the bringing about of supersaturation in the concentrated lactic acid solution by evaporation of water without supplying heat. The evaporation of water has two effects: (a) the temperature of the concentrated lactic acid solution becomes lower and (b) the concentration of the acid increases. Both effects lead to a decrease in the solubility and an increase in the supersaturation.

Crystallization step (c) is preferably carried out according to the invention by means of adiabatic crystallization or cooling crystallization, in particular by means of adiabatic crystallization. Seed crystals are preferably added to the concentrated lactic acid solution in the crystallization.

The lactic acid which is crystallized out can then be separated by the known methods for solid-liquid separation from the remaining liquid, or mother liquor.

Examples of suitable separation techniques for separating the lactic acid crystals from the mother liquor are centrifugation, decanting, filtration, separation by means of one or more washing columns, or a combination of two or more of these techniques. In the context of the invention it has been found that centrifugation and separation with one or more washing columns is particularly appropriate.

The mother liquor which is obtained still contains considerable quantities of lactic acid. For optimal process management it is therefore preferable to feed this mother liquor back into the process.

After isolation, the lactic acid crystals which are obtained are directly dissolved in a suitable solvent, usually water, in order to prevent coagulation of the hygroscopic lactic acid crystals occurring. The concentration of the lactic acid solution so obtained can in principle have any desired concentration. In practice this will usually vary from 30 to 95%. Concentrations commonly occurring on the market are 80-90%.

The invention also relates to an α-hydroxy acid or an α-hydroxy acid solution with a chiral purity of at least 99% and a colour of not more than 10 APHA units, with the α-hydroxy acid or the α-hydroxy acid solution having an acceptable odour, in particular for pharmaceutical applications. In the case of an α-hydroxy acid solution the solvent is preferably water. The chiral purity, if applicable, is preferably at least 99%, in particular at least 99.5%, which corresponds to 99% enantiomeric excess (ee) or higher. Most preferable is lactic acid, or the solution thereof, whose chiral purity is at least 99.8% (i.e. at least 99.6% ee).

The α-hydroxy acid or the α-hydroxy acid solution also meets the following requirements:
 alcohol content: not more than 250 ppm (alcohol is methanol, ethanol or other alcohol, as alcohol as such or in the form of a lactate).
 total nitrogen: not more than 5 ppm.
 total sugar: not more than 100 ppm.
 organic acids (other than lactic acid): not more than 250 ppm.

With regard to odour the α-hydroxy acid or the α-hydroxy acid solution possesses a considerable improvement for application in foods and a higher chemical purity than the products according to the prior art.

The α-hydroxy acid according to the invention can be both (S)-α-hydroxy acid and (R)-α-hydroxy acid, depending on the microorganism which is used in the fermentation.

Because of their high chiral purity both the (S)-α-hydroxy acid and the (R)-α-hydroxy acid or the solutions thereof can very suitably be applied for chiral syntheses. The chirally pure (S)-α-hydroxy acid or solutions thereof are also very suitable for being applied in pharmaceutical preparations.

The invention therefore also relates to a pharmaceutical preparation which contains the (S)-α-hydroxy acid described above or the (S)-α-hydroxy acid. The invention is now illustrated by means of the following example.

EXAMPLE 1

An (S)-lactic acid solution as obtained on an industrial scale with the method which is described in Netherlands Patent Application 1013265 is used as the starting material. This method comprises fermentation to lactic acid, processing of the fermentation medium by acidification and removal of the salts so formed. This gives a lactic acid solution which is then subjected to an extraction step according to step (a) of the method according to the present invention. After the extraction the solution is treated with activated charcoal to remove any extraction agent present. The properties of the lactic acid solution were as follows:

| | |
|---|---|
| Total acid | 42.1% |
| Monomeric acid | 41.2% |
| Colour (fresh) | 132 APHA |

The solution is then concentrated using a KDL-4 short-path distiller (conditions: oil bath 130° C., feed rate 10 ml/min, pressure 100 mbar, rotor speed 250 r.p.m. cooling water is tap water). The lactic acid concentration of the deposit was about 91% by weight, calculated in terms of the deposit.

The crystallization was performed as follows. 327 g of the concentrated lactic acid was put into a three-necked round-bottomed flask and the flask was placed in a thermostat bath. At 31° C. the solution was inoculated with 0.12 g of a suspension of very small lactic acid crystals. The flask was cooled to 30° C. while stirring, and the seed crystals were left to grow for 20 min at this temperature. The suspension was further cooled as follows: from 30° to 26° C. in 2 hours, followed by cooling to 15° C. in 3 hours. After crystallization the suspension was centrifuged (Sieva laboratory centrifuge, Hermle), giving 150 g of lactic acid crystals. This means that the yield is 54% (calculated in terms of lactic acid). The crystals were dissolved in a small quantity of water, giving a solution of 90% by weight lactic acid. The colour (fresh) was 8 APHA and 15 APHA (after heating), respectively.

The invention claimed is:

1. A method for the purification of an α-hydroxy acid on an industrial scale, comprising:
 (a) subjecting an aqueous stream containing mainly α-hydroxy acid [1] and contaminants from a fermentation process to an extraction step, with the formation of an aqueous phase containing mainly α-hydroxy acid [2],
 (b) concentrating the aqueous phase containing mainly α-hydroxy acid [2] by means of evaporation of water under reduced pressure, with the formation of a concentrated α-hydroxy acid solution in water [3], and
 (c) subjecting the concentrated α-hydroxy acid solution [3] to a crystallization, with formation of pure α-hydroxy acid [4], where
  (i) the concentrated α-hydroxy acid solution [3] is directly cooled in a melting crystallization device, and/or
  (ii) the concentrated α-hydroxy acid solution [3] is diluted with water and crystallization is brought about in one or more cooling crystallization devices and/or evaporative crystallization devices, and/or
  (iii) crystallization is brought about in one or more adiabatic crystallization devices.

2. The method according to claim 1, wherein the α-hydroxy acid is lactic acid or glycolic acid.

3. The method according to claim 2, wherein the α-hydroxy acid is lactic acid.

4. The method according to claim 1, wherein the aqueous phase containing mainly α-hydroxy acid [2] contains 0.1 to 25% by weight α-hydroxy acid and has a colour of not more than 100 APHA units.

5. The method according to claim 1, wherein the aqueous phase containing mainly α-hydroxy acid [2] has a colour of not more than 100 APHA units.

6. The method according to claim 1, wherein the aqueous phase containing mainly α-hydroxy acid [2] contains 30 to 80% by weight α-hydroxy acid, calculated in terms of the whole stream, with this stream having a colour which is not more than 200 APHA units.

7. The method according to claim 1, wherein step (a) comprises the following component steps:
   (i) subjecting an aqueous stream containing mainly α-hydroxy acid [1] to a first extraction step, where the aqueous stream containing mainly α-hydroxy acid [1] is brought into contact with a stream which is mainly insoluble in water and which contains an extraction agent [5], with the formation of an organic phase containing mainly α-hydroxy acid and extraction agent [6] and a first aqueous phase containing mainly contaminants [7], and
   (ii) subjecting the organic phase containing mainly α-hydroxy acid and extraction agent [6] to a second extraction step, where the organic phase containing mainly α-hydroxy acid and extraction agent [6] is brought into contact with an aqueous stream [8], with the formation of an aqueous phase containing mainly α-hydroxy acid [2] and an organic phase containing mainly extraction agent [9], with the organic phase containing mainly extraction agent [9] being fed back to step (i).

8. The method according to claim 7, wherein the organic phase containing mainly α-hydroxy acid and extraction agent [6] is subjected to a washing step with water before step (ii), with formation of an aqueous phase containing mainly contaminants [10].

9. The method according to claim 8, wherein the aqueous phase containing mainly contaminants [10] is fed back into the process before step (a).

10. The method according to claim 7, in which step (i) is carried out at atmospheric pressure and at a temperature of 0° to 60° C.

11. The method according claim 7, wherein step (i) is carried out at atmospheric pressure and a temperature of 60° to 100° C.

12. The method according to claim 7, wherein the volumetric ratio of the aqueous stream containing mainly α-hydroxy acid [1] and the mainly water insoluble stream containing the extraction agent [5] is between 20:1 and 1:20.

13. The method according to claim 7, wherein step (ii) is carried out at a pressure of 1 to 10 bar and a temperature of 100° C. to 180° C.

14. The method according to claim 7, wherein the volumetric ratio of the organic phase containing mainly α-hydroxy acid and extraction agent [6] and the aqueous stream [8] is between 20:1 and 1:20.

15. The method according to claim 1, wherein the extraction step comprises an extraction agent comprising an amine or a hydrocarbon.

16. The method according to claim 15, wherein the extraction agent further comprises an alcohol and/or a ketone.

17. The method according to claim 16, wherein the extraction agent contains 40 to 75% by weight amine, 5 to 60% by weight hydrocarbon and 0 to 25% by weight alcohol and/or ketone.

18. The method according to claim 1, wherein the concentrated α-hydroxy acid solution [3] has a total acid content of at least 70% by weight, calculated in terms of the whole feed stream, and a ratio of the α-hydroxy acid enantiomers which is not equal to 1.

19. The method according to claim 1, wherein step (b) is carried out in one or more falling-film evaporators and/or thin-film evaporators and/or smeared-film evaporators.

20. The method according to claim 1, wherein step (b) is carried out at a pressure from atmospheric pressure to 0.1 bar and at a temperature of 25° to 140° C.

21. The method according to claim 1, wherein the crystallization step (c) is carried out in one or more cooling crystallization devices, evaporative crystallization devices and/or adiabatic crystallization devices.

22. The method according to claim 1, wherein the product stream from the crystallization step (c) is separated into a mother liquor and α-hydroxy acid crystals by means of a solid-liquid separation.

23. The method according to claim 1, wherein the chiral purity of the monomeric hydroxy acid present in the aqueous stream containing mainly α-hydroxy acid [1] is at least 90%.

24. The method according to claim 1, wherein the aqueous stream containing mainly α-hydroxy acid [1] is obtained from fermentatively prepared α-hydroxy acid.

25. The method according to claim 22 in which the solid-liquid separation is conducted by centrifugation, use of one or more washing columns, or both.

26. The method according to claim 23, wherein the chiral purity of the monomeric hydroxy acid present in the aqueous stream containing mainly α-hydroxy acid [1] is at least 95%.

* * * * *